US010641843B2

(12) United States Patent
Israelowitz et al.

(10) Patent No.: US 10,641,843 B2
(45) Date of Patent: May 5, 2020

(54) EMBEDDED CRYSTAL CIRCUIT FOR THE DETECTION OF WEAK ELECTRICAL AND MAGNETIC FIELDS

(71) Applicants: Meir Israelowitz, Toronto (CA); Herbert Peter von Schroeder, Toronto (CA); Syed Rizvi, Lake Mary, FL (US); Chris Holm, Wuppertal (DE); Christoph Gille, Hohen Herrendorf (DE)

(72) Inventors: Meir Israelowitz, Toronto (CA); Herbert Peter von Schroeder, Toronto (CA); Syed Rizvi, Lake Mary, FL (US); Chris Holm, Wuppertal (DE); Christoph Gille, Hohen Herrendorf (DE)

(73) Assignee: BIOMIMETICS TECHNOLOGIES, INC., Toronto, Ontario (CA)

( * ) Notice: Subject to any disclaimer, the term of this patent is extended or adjusted under 35 U.S.C. 154(b) by 227 days.

(21) Appl. No.: 13/905,564

(22) Filed: May 30, 2013

(65) Prior Publication Data
US 2019/0146042 A1    May 16, 2019

Related U.S. Application Data

(63) Continuation-in-part of application No. 12/383,553, filed on Mar. 26, 2009, now abandoned.

(51) Int. Cl.
*G01R 33/02* (2006.01)
*G01R 33/12* (2006.01)

(52) U.S. Cl.
CPC ......... *G01R 33/02* (2013.01); *G01R 33/1269* (2013.01)

(58) Field of Classification Search
CPC ...................................................... G01R 33/02
See application file for complete search history.

(56) References Cited

U.S. PATENT DOCUMENTS 8,077,152 B2 * 12/2011 Wohlgenannt ......... G01R 33/09
324/244
2002/0076837 A1    6/2002 Hujanen et al. ................ 438/3
(Continued)

OTHER PUBLICATIONS

Godovsky et al.; Magnetic properties of polyvinyl alcohol-based composites containing iron oxide nanoparticles; Advanced materials for optics and electronics; Jul. 1999; pp. 87-93.*
(Continued)

*Primary Examiner* — Jay Patidar
(74) *Attorney, Agent, or Firm* — Greer, Burns & Crain, Ltd; Steven P. Fallon

(57) ABSTRACT

The invention relates to a circuit or microchip for the detection of poor sources of (or very weak) electrical and/or magnetic fields. In one embodiment a device of the present invention includes a microchip consisting of a plate with a plurality of cells, each cell includes a crystal suspended in a semiconducting polymer and piece of metal wire. The cell is insulated by another polymer. A voltage is applied to parallel wires running on each side of the cell, thus inducing a first (or static, or initial) voltage when measured from the cell to the wire. Changes in magnetic or electrical fields are detected by noting a change in voltage from the cell, which is caused by the crystal changing orientation due to the change in the field the circuit is subjected to.

9 Claims, 8 Drawing Sheets

(56) References Cited

U.S. PATENT DOCUMENTS

| | | | |
|---|---|---|---|
| 2003/0129763 A1* | 7/2003 | Chamberlain | G01N 11/00 436/149 |
| 2005/0089803 A1 | 4/2005 | Bouaidat et al. | 430/312 |
| 2007/0197953 A1* | 8/2007 | Slade | A61K 41/00 604/19 |
| 2008/0223820 A1 | 9/2008 | Wu et al. | 216/13 |
| 2009/0057839 A1 | 3/2009 | Lewis et al. | 257/618 |
| 2009/0152657 A1 | 6/2009 | Suh et al. | 257/421 |
| 2009/0155932 A1 | 6/2009 | Suh et al. | 438/3 |
| 2009/0186770 A1 | 7/2009 | Shi et al. | 506/6 |
| 2010/0136669 A1* | 6/2010 | Weekamp | G01N 27/745 435/287.2 |
| 2016/0169988 A1* | 6/2016 | Sirringhaus | H01L 43/065 324/251 |

OTHER PUBLICATIONS

Abdou, Mohamed and Holdcrof, Steven, "Solid-state photochemistry of Pi-conjugated poly(3-alkylthiophenes)", 1995, Can J Chem pp. 1893-1901.

"Quantum Physics of Atoms, Molecules, Solids, Nuclei, and Particles." Quantum Physics of Atoms, Molecules, Solids, Nuclei, and Particles, by Robert Martin Eisberg and Robert Resnick, Wiley, 2017, pp. 533-545.

Kraus, John D. "Electromagnetics." Electromagnetics, 4th ed., McGraw-Hill Education, 1992, p. 167.

"First Course in Solid State Physics." First Course in Solid State Physics, by Ashok Rao, Asiatech Publishers Inc, 2000, pp. 175-211.

"Conducting Polymers a New Era in Electrochemistry." Conducting Polymers A New Era in Electrochemistry, by Inzelt György, Springer Berlin, 2014, pp. 7-60.

"Conducting Polymers a New Era in Electrochemistry." Conducting Polymers A New Era in Electrochemistry, by Inzelt György, Springer Berlin, 2012, pp. 149-171.

"Chapter 7." Solid State Physics, by H. E. Hall, Publisher Not Identified, 1971, pp. 198-217.

"Chapter 10." Mineral Science: (after James D. Dana), by Cornelis Klein and Barbara Dutrow, J. Wiley, 2008.

Kraus, John D. "Electromagnetics." Electromagnetics, 4th ed., McGraw-Hill Education, 1992, p. 230-231,302-304.

Kraus, John D. "Electromagnetics." Electromagnetics, 4th ed., McGraw-Hill Education, 1992, p. 220.

"Chapter 6." Mineral Science: (after James D. Dana), by Cornelis Klein and Barbara Dutrow, J. Wiley, 2008, pp. 109-119.

Ferry, John D. Viscoelastic Properties of Polymers. J. Wiley, 1980. , p. 80-641.

Kraus, John D. "Electromagnetics." Electromagnetics, 4th ed., McGraw-Hill Education, 1992, p. 308-309.

"Chapter 8." Solid State Physics, by H. E. Hall, Publisher Not Identified, 1971.

* cited by examiner

EMBEDDED CRYSTAL CIRCUIT FOR THE DETECTION OF WEAK ELECTRICAL AND MAGNETIC FIELDS

PRIORITY CLAIM

This is a Continuation-in-Part (CiP) application to the pending, non-provisional utility patent application Ser. No. 12/383,553 filed on 2009 Mar. 26. The present application is based on and claims priority from this application, the disclosure of which is hereby expressly incorporated herein by reference.

BACKGROUND

The invention relates to a Microchip for the detection of poor sources of electrical and/or magnetic fields.

Poor sources of electrical and/or magnetic fields are situated not only in electrical circuits but also in metallic items located in the radiation of transmitters of all kinds. Especially of interest are sources of electrical voltages coming from human or animal bodies because they show places of irregularities in these bodies. These irregularities have a weak electrical voltage (termed herein as a "poor source of an electrical or magnetic field"), but the corresponding electrical field could be detected or measured if it is not masked or super-imposed by a stronger electrical field or fields.

To detect such weak or poor electrical sources hidden in a body is a difficult problem: However, the present invention provides a solution for this.

SUMMARY OF THE INVENTION

The invention creates a device consisting of a microchip for the detection of sources of electrical and/or magnetic fields. The microchip, according to the present invention includes a plate with parallel rows of recesses or grooves, in each recess is at least one cell, in each cell there is a crystal with inherent magnetic activity or magnetic field, between the rows are one or more wires (aligned parallel to the grooves or recesses) and the rows of wires are coupled to lead wires, which are, in turn, connected with a voltage source and/or a voltmeter. The whole surface of the plate with the crystals in the recesses and the associated wires are embedded in a layer of a polymer, as would be generally understood in this art.

The device of the present invention also utilizes a microchip adapted to detect sources of electrical and/or magnetic fields wherein the device consists of a plate with parallel rows of recesses (or grooves), in each recess is a crystal with a magnetic activity embedded in a semiconducting polymer, in each recess is on the ground a layer of thin metal, between the rows are one or more wires connected with a voltage source and one or more wires connected on one end with the metal layer on the ground of each recess or groove and on the other end with a voltmeter.

To detect an electrical or magnetic field, this microchip should be brought so close as possible to the object to investigate and the voltmeter will show the biggest voltage if the microchip is nearest to the sought location of the source of the electrical field. By turning the microchip at a location of the highest measured voltage it is possible to get further information about the direction of and the source of the electrical and/or magnetic field.

One set of parallel wires can be connected with a current source. A second set of parallel wires can relate to the voltmeter. It is also possible to connect the source of current and the voltage with the same parallel wires if the source of current is highly resistive.

A microchip device for the detection of poor sources of electrical and/or magnetic fields, the device comprises a plate comprising at least two parallel rows of recesses wherein each respective recess comprises a crystal having magnetic activity, one or more wires coupled to the plate between each at least two parallel rows of grooves or recesses and each one or more wires being adapted to be in inductive electrical communication with an associated crystal. Each associated crystal comprises a material selected from the group consisting of Ferroso-Ferric Oxide, Ferosic Oxide, or Ferroso Sulfur Oxide. The microchip further includes a power source in in electrical communication with the one or more wires to create a voltage in those wires. And, a voltmeter detects changes in voltage from a first state to a second state by measuring between the wires and the crystal.

This microchip further includes at least four parallel rows of recesses or grooves wherein each respective row comprises four grooves to create a four by four array having sixteen cells. Each cell comprises a piece of wire coupled to a semiconducting polymer and a crystal suspended in the semiconducting polymer.

A method of detecting poor sources of electrical and/or magnetic fields, the method comprises providing a microchip comprising at least one cell and at least one set of parallel wires to the cell, the parallel wires having a voltage applied. The cell includes a piece of wire coupled to a semiconducting polymer and a crystal suspended in the semiconducting polymer. A voltmeter is used to detect change in voltage across the circuit.

DRAWINGS

Figure 9:
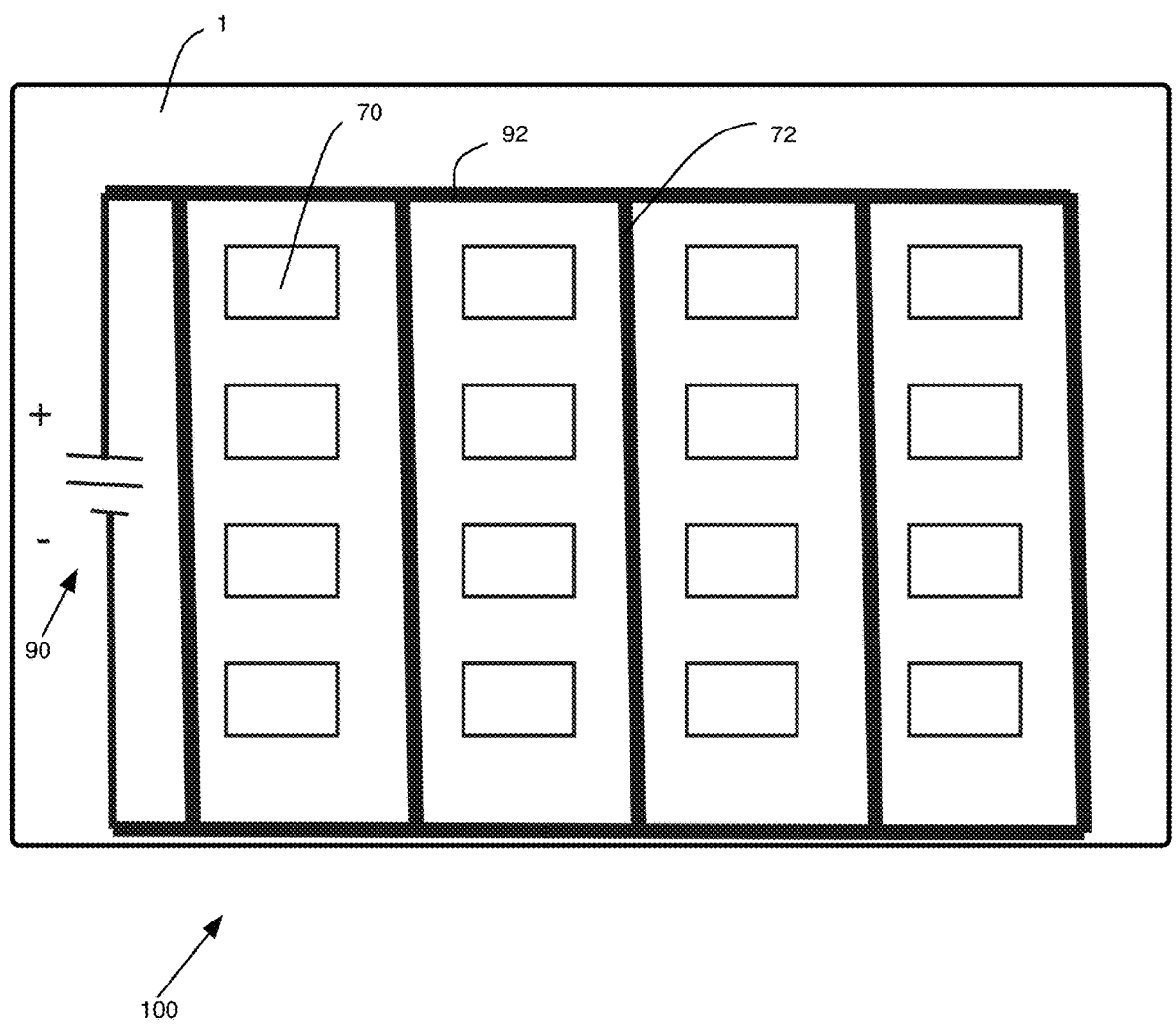
FIG. 9 is a top view of a system according to the present invention.
Figure 10:
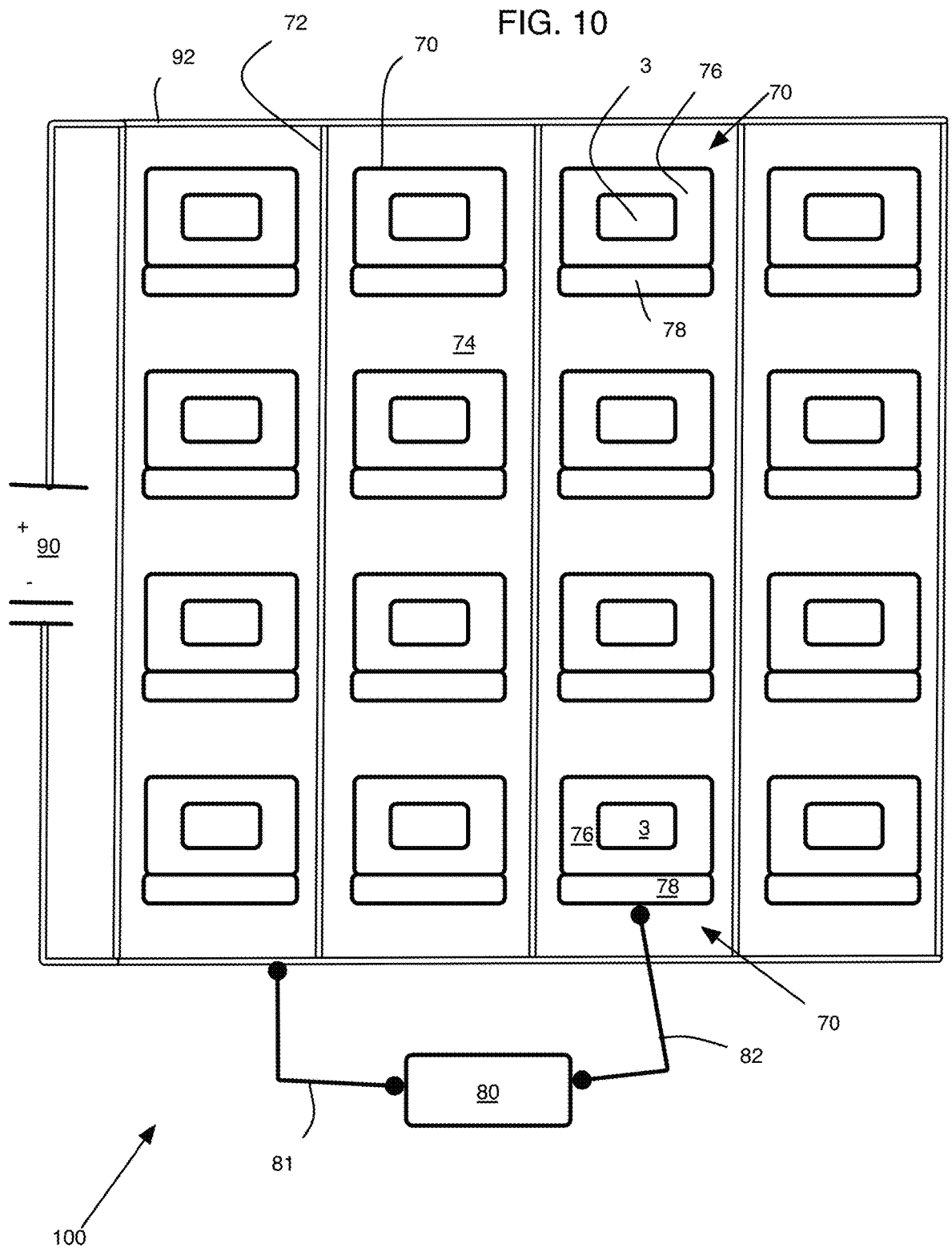

FIG. 10 a top view showing additional components of the system of FIG. 9.

Figure 7:
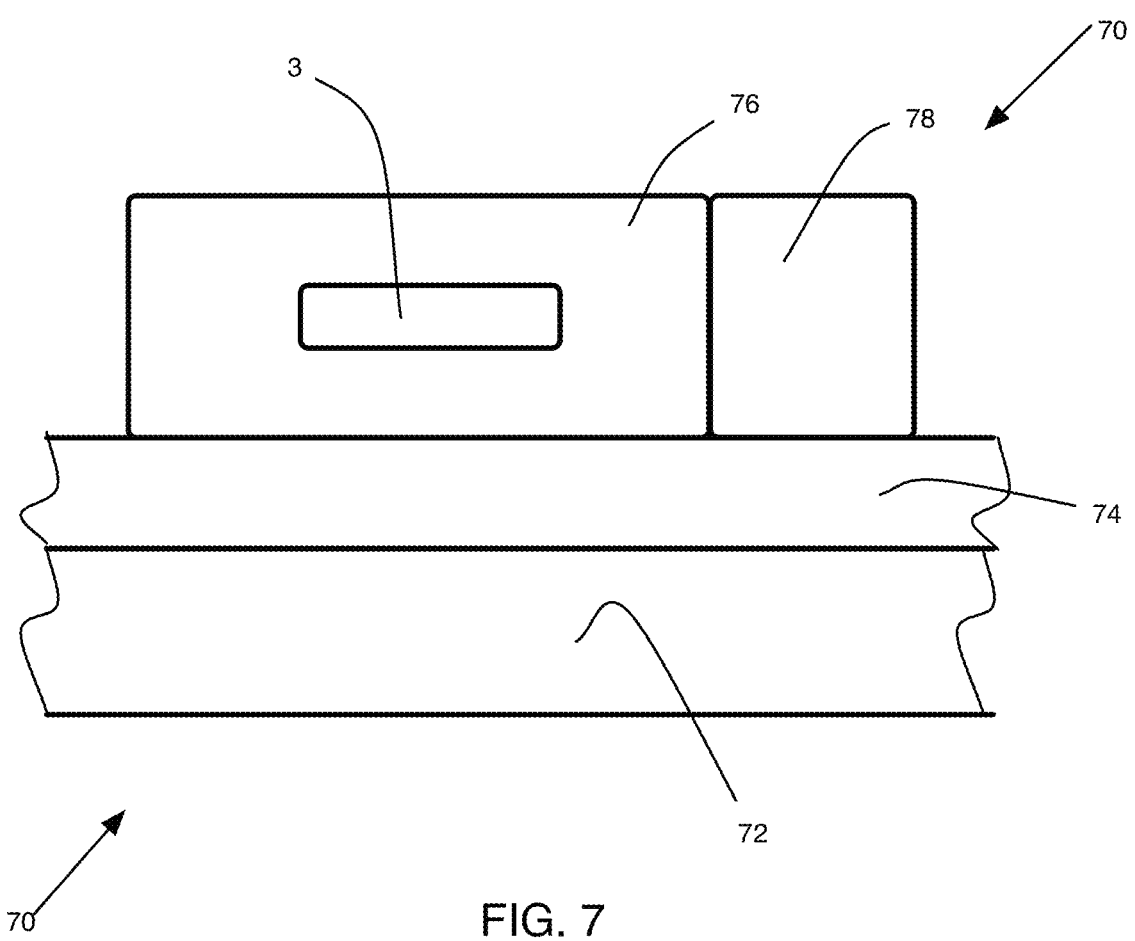
FIG. 7 is a detail view of a cell consisting of a crystal, a semiconducting polymer, and a piece of wire according to a system of the present invention.
Figure 11:
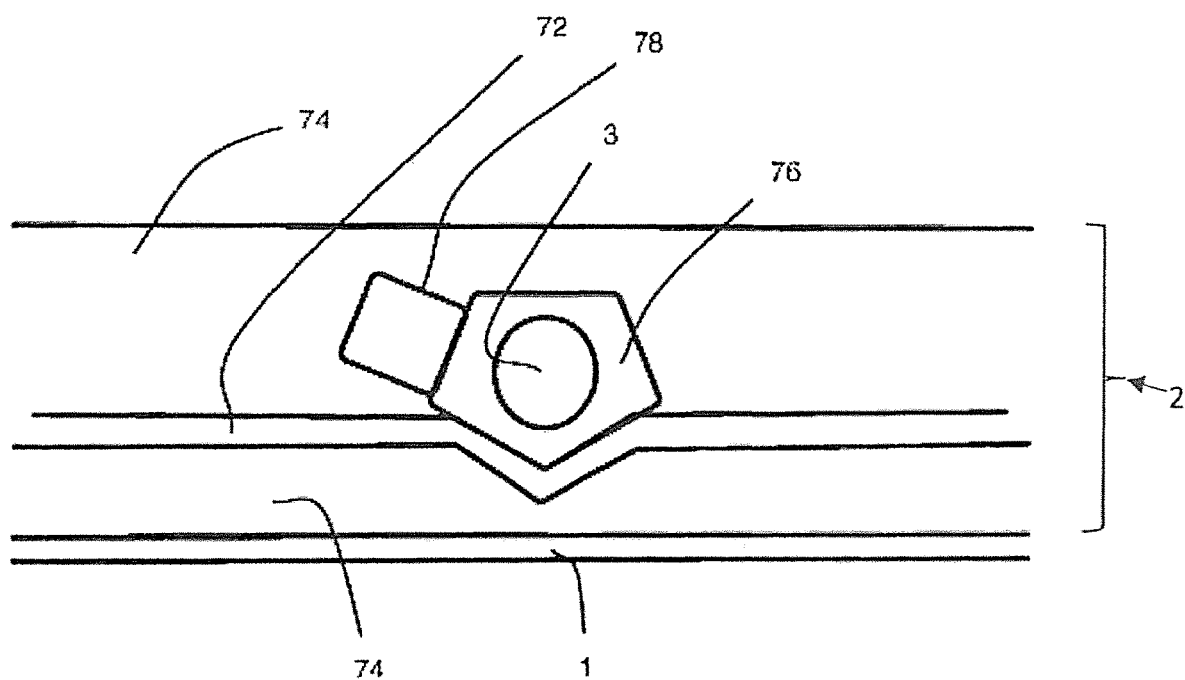
Figure 12A:
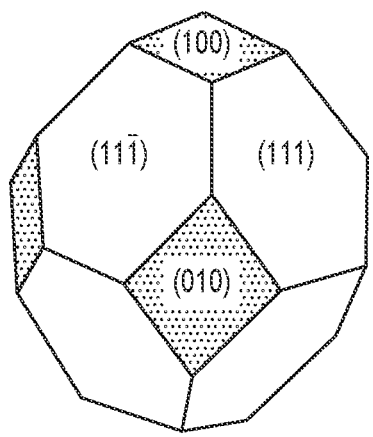
Figure 12B:
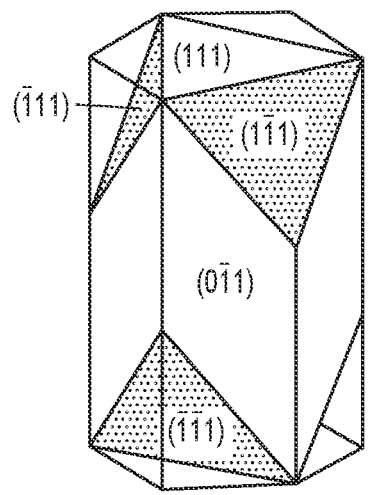
Figure 12C:
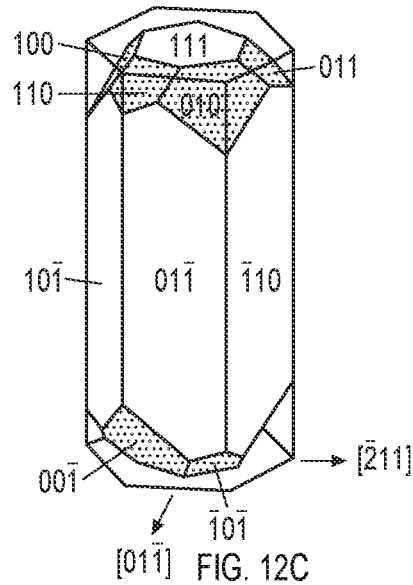
Figure 12D:
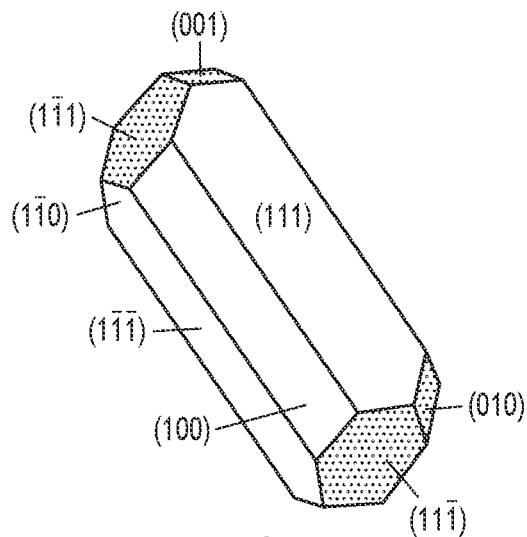
Figure 12E:
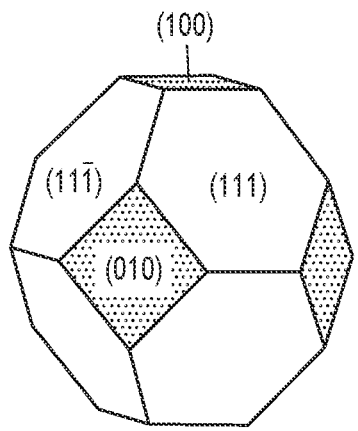
Figure 12F:
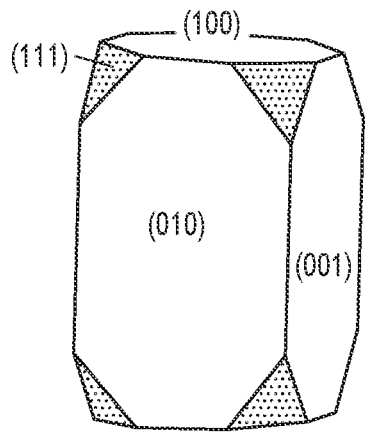

FIG. 11 is a partial side view detailing the cell of FIG. 7 in relation to the system of the present invention.

FIGS. 12A-12F are illustrations of various crystals contemplated by the present invention.

DESCRIPTION OF THE INVENTION

Possible preferred embodiments will now be described with reference to the drawings and those skilled in the art will understand that alternative configurations and combinations of components may be substituted without subtracting from the invention. Also, in some figures certain components are omitted to more clearly illustrate the invention.

The microchip consists of a circuit board, which is a metal plate 1 upon which a microchip system 100 is built. In this example, the chip consists of an array of four rows and four columns (see, e.g. FIG. 9) forming sixteen individual cells 70. Other configurations are also contemplated including an array of eight rows and eight columns.

Figure 1:
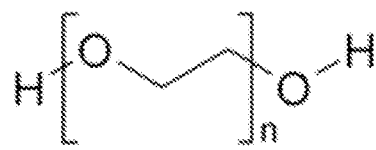
FIG. 1 is an illustration of a chemical compound of a suitable insulating polymer contemplated by the various embodiments of the present invention.
Figure 2:
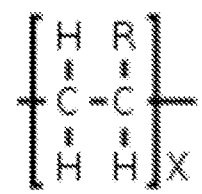
FIG. 2 is an illustration of a chemical compound of a suitable insulating polymer contemplated by the various embodiments of the present invention.

However, in this preferred embodiment, as FIGS. 9 and 10 illustrate, the chip consists of five grooves, in each groove is at least one wire 72 running parallel to it and each of these wires are in electrical communication with a source 90 by means of a pair of cooperating leads 92. The leads 92 and wires 72 are embedded in a polymer 74, which adheres to the plate 1. The metal wire 72 is arranged to be parallel to the groove. (See FIG. 2). The polymer 74 that embeds the wire is a polymer of a jelly-like consistency, which is also known in this art as a gel and can have properties ranging from soft and weak to hard and toughs. Gels are defined as a substantially dilute cross-linked system, which exhibits no flow when in the steady-state (see e.g. Ferry, John D., 1980. "Viscoelastic Properties of Polymers" New York: Wiley, the entire reference is hereby incorporated by this reference as if set out fully herein). By weight, gels are mostly liquid, yet they behave like solids due to a three-dimensional cross-linked networks within the liquid. It is the crosslinking within the fluid that gives a gel its structure (hardness) and contributes to the adhesive stick (tack). In this way gels are a dispersion of molecules of a liquid within a solid in which the solid is the continuous phase and the liquid being the discontinuous phase? The polymer consider are hydrogels: is a network of polymer chains that are hydrophilic, sometimes found as a colloidal gel in which water is the dispersion medium. Once contemplated example suitable for use in the present invention is Polyethylene glycol (PEG) (See FIG. 1), or PolyAMPS (a trademark of Lubrizonl Corporation, See e.g. FIG. 2), for example.

Figure 3:
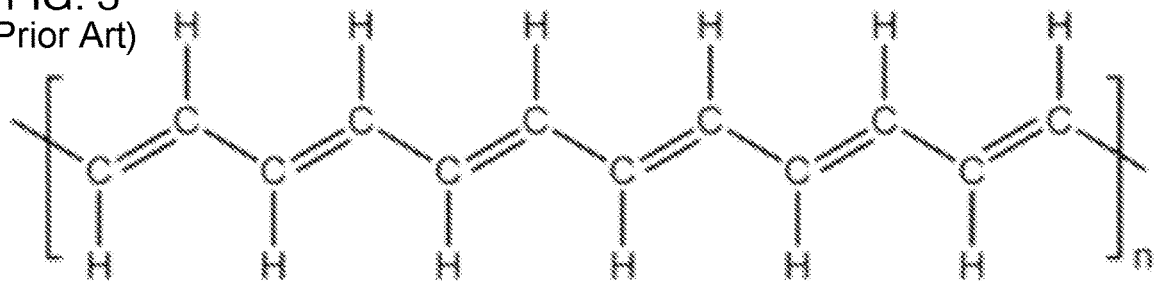
FIG. 3 is an illustration of a chemical compound of a suitable semiconducting polymer contemplated by the various embodiments of the present invention.
Figure 4:
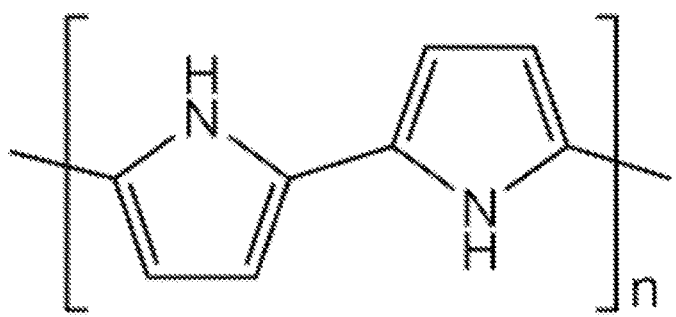
FIG. 4 is an illustration of a chemical compound of a suitable semiconducting polymer contemplated by the various embodiments of the present invention.
Figure 5:
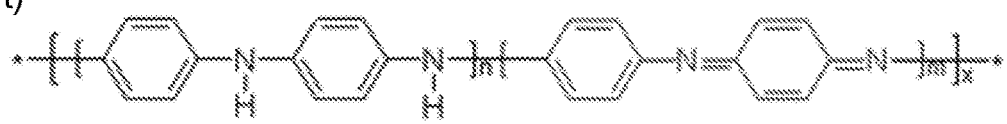
FIG. 5 is an illustration of a chemical compound of a suitable semiconducting polymer contemplated by the various embodiments of the present invention.

A cell is defined by the space defined by each intersection of two pairs of grooves in array (in this preferred embodiment, as FIGS. 9 and 10 show, the array is a four by four array of cells), contains an amount of a semiconducting polymer 76 of a jelly-like consistency and in this a single crystal 3 arranged on top of the piece of metal 78 (See FIG. 7). This semi-conducting polymer 76 or jelly is known as an Intrinsically conducting polymer (ICP), which are a class of organic polymers that conduct electricity (See, e.g. lnzelt, Gyorgy, in Scholz, F. "Conducting Polymers: A New Era in Electrochemistry", Monographs in Electrochemistry. Springer (2008), the entire reference is hereby incorporated by reference as if set out fully herein). Examples of these semiconducting polymers include Polyacetylene (see FIG. 3), or Polypyrrole (PPy) (FIG. 4), or Polyaniline (PANT) (FIG. 5), for example.

The crystal 3 is a homogenous solid substance with smooth planar surfaces with a regular geometry shape. The crystal is sensitive to magnetic fields and the semiconducting polymer 76 is a conductor of electrons. Electrons are distributed in specific orbits of discrete energy levels (i.e. shells). Crystals are formed based on the properties of the element from which they are based. Using the periodic table, valance electrons (the electrons available for chemical bonding so that atoms can combine to form crystal solids) can be influenced by an electric and/or magnetic field. Ions of an element occur when there is an excess or deficiency of electrons when compared to the number of protons, this is also known as the valance or oxidation state. The electrons in outermost shells are valance electrons, when one or more electrons are lost from electron configuration of an atom a cation is formed (net positive charge +) and when is added anion (negative charge −). The table of metals classify two types of metals; those that have the tendency to add (electrons) and those that loose (electrons). In the case of crystals, the valance electrons have the tendency to bring other atoms to proximity. The ionic bond forms when one or more electrons in the valance shell of an atom are transferred to valance to another atom. However, electrons cannot be just lost to maintain electrical neutrality, the electrons lost most be selected deliberately (the present invention contemplates a preferred crystal formed from $FeO2$ and $FeSO2$): Therefore, the electron lost by the Fe-atom must also be suitable for electron transfer. (See, e.g., Klein, Cornellis and Dutrow, Barbara, (2007), "Mineral Science", 23 Ed., John Wiley & Sons; and Eisberg, Robert and Resnick, Robert, (1974), "Quantum Physics of Atoms, Molecules and Particles", John Wiley & Sons, these references are hereby fully incorporated herein by reference as if fully set out herein).

Figure 6:
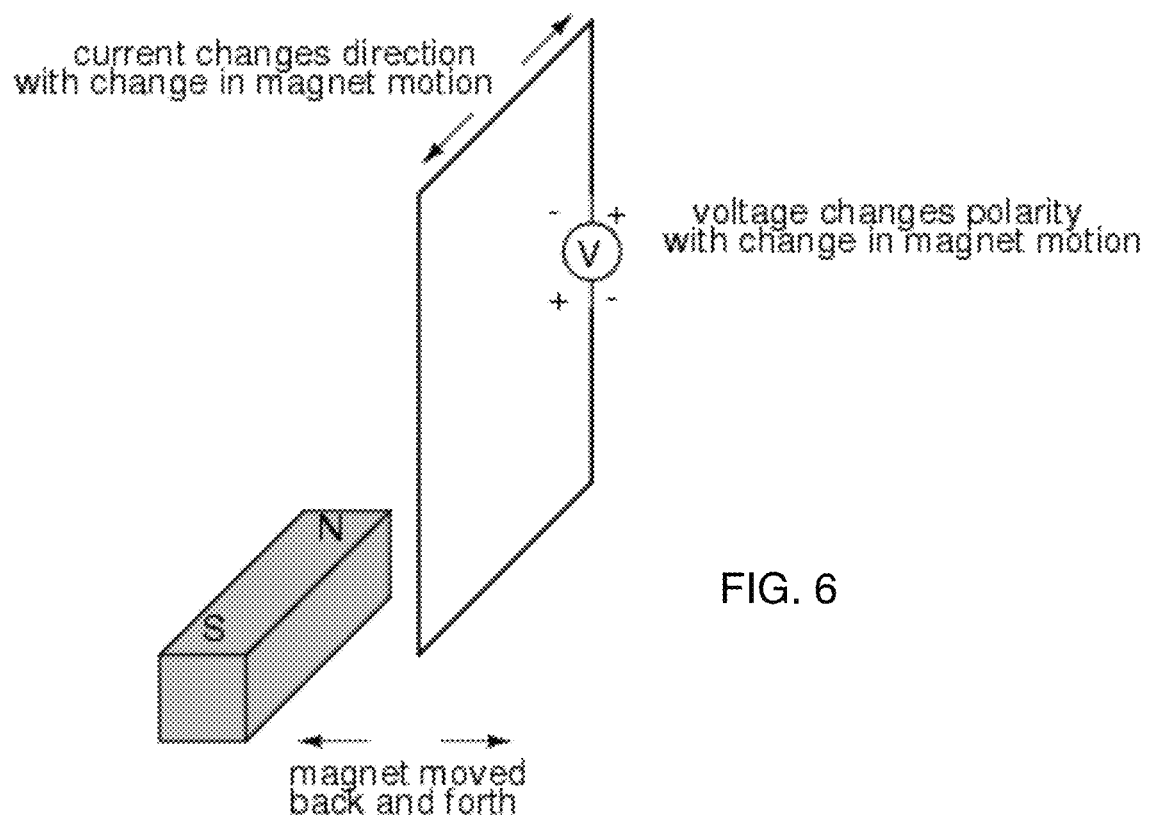
FIG. 6 is an illustration of magnetic and electrical induction.

FIG. 10 illustrates this sixteen-cell, four by four array having lead wires 92 in electrical communication with a source 90 and electrically coupling to groove wires 72. Each cell 70 consists of a piece of wire 78 and a crystal 3 surrounded by a semiconducting gel 76. Each cell 70 is surrounded by a polymer 74, which is the same polymer that encases the wires 72 and leads 92. A voltmeter 80 is connected via connections 81 and 82 to either the lead 92 or wire 72 at one input, and the second input connects to the wire 78 of the cell 70 of interest. Referring now to FIG. 6, which depicts a well-understood model of induction, a current is introduced into the circuit of FIG. 10 through from the source 90 through the leads 92 and wires 72. In turn, a current is induced in the wires 78, and this causes the crystals 3 to alter states. Conversely, should the crystals 3 change states due to an outside electric influence, the surplus electron from the crystal 3 would travel through the semiconducting polymer 76 to the wire 78, and thus inducing a current in the wire 72. This current could then be detected by a voltmeter 80 or at the source 90.

FIG. 7 details one cell 70 having a crystal 3 embedded in a semiconducting polymer 76 and the adjacent piece of wire 78, which, in this view, runs into, or orthogonally, to the sheet of paper. And wire 72 runs left to right, or parallel with the face of the sheet of paper. A polymer 74 insulates the wire 72 from the piece of metal 78 (wire 78). This polymer 74 surrounds t h e entire cell 70, although this figure omits this feature for clarity.

Figure 8:
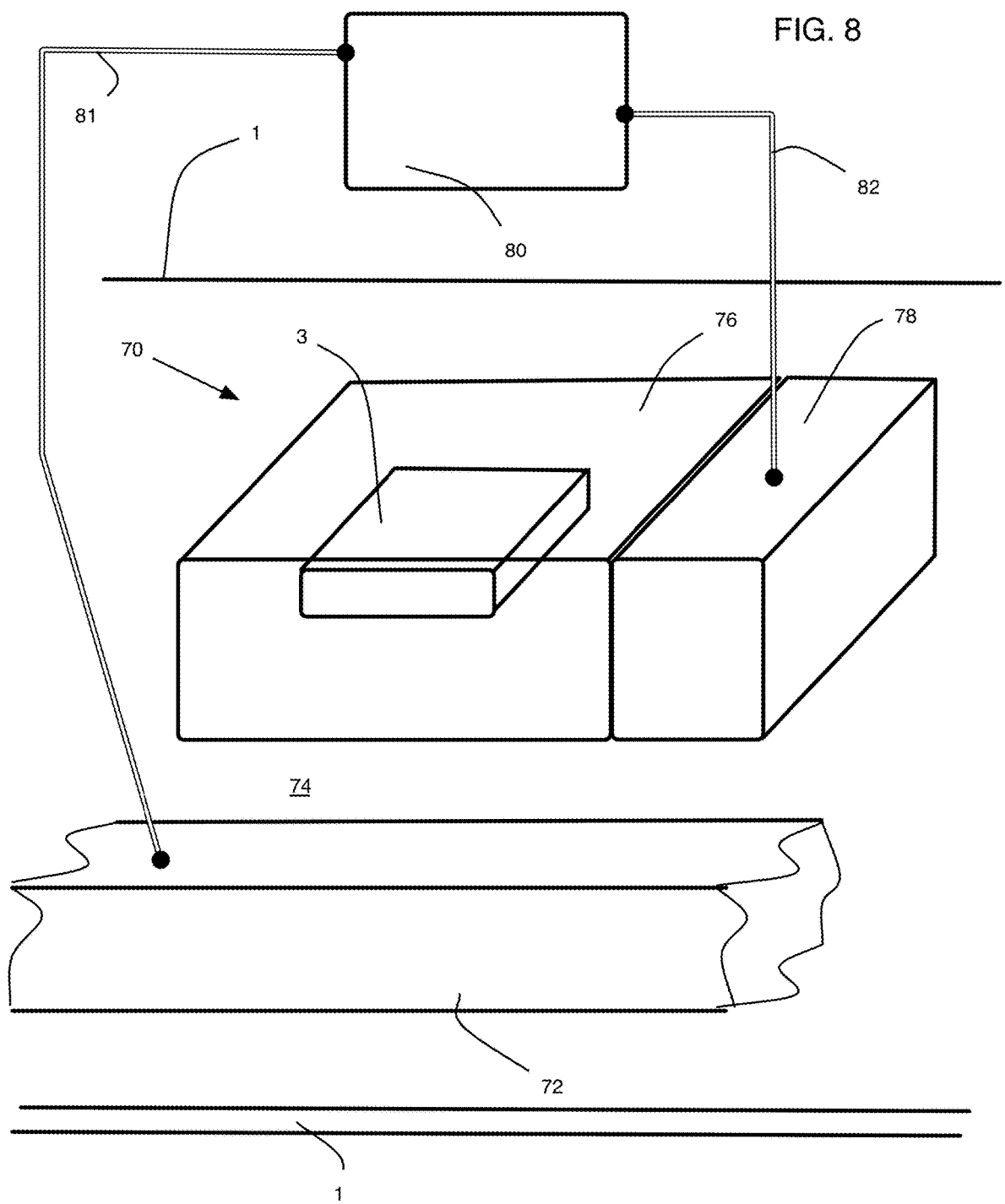
FIG. 8 shows additional elements in relation to the cell of FIG. 7.

FIG. 8 adds additional elements to the cell of FIG. 7. In FIG. 8, a voltmeter is connected to a cell 70 to detect current between the crystal 3 and wire 72. The metal plate 1 of the circuit board carries the polymer 74, which surrounds and insulates each element. The wire 72 runs left to right on the face of the sheets and the piece of wire 78 runs orthogonal to that wire, or in and out orthogonally to the face of the sheet of paper.

FIG. 11 details a groove 2 of the present invention. The wire 72 runs parallel to the groove 2. In this view the groove runs from left to right of the sheet of paper. The piece of wire 78 extends orthogonal to the sheet of paper, perpendicular to the wire 72.

FIGS. 12A-12F show graphical representations of the relationship of the morphology of crystals and the choice of crystallographic axis. The numbers are notations related to the Miller Index, as would be well understood by those of ordinary skill in this art. A crystal 3 includes a plurality of faces, a face consist of a series of whole numbers that have been derived from the intercepts (i.e. are the place where crystallographic axis (or axes) it intersects), by inverting and if necessary, the subsequent clearing of fractions.

Referring generally to FIGS. 6-12, the microchip system 100 works as follows: The wires 72 produce an electrical and magnetic field from source 90 via leads 92. In this electrical field the crystals 3 lay in a distant orientation (a first orientation). Because of the jelly-like consistency of the semiconducting polymers 76 in which the crystals 3 are embedded, the crystals are free to alter shape and/or orientation should they gain or lose a valence electron as a result in a change to the magnetic field or electrical field of the system. Thus, should an outside influence alter the first orientation of the crystals, or more particularly, alter the magnetic field of the system, the crystals would gain or loose an electron in response and thereby change shape. This turning to another orientation (a second orientation, See FIG. 12) if the field is changed produces an electron in the semiconducting jelly polymer 76. The produced electrons travel through the wires 72 to the collector rail 5 and can be measured by the voltmeter 80.

Outer influences are other electrical or magnetic fields superposing the field produced by the wires 72. These fields can be produced, for example, in a human or animal body. For example, a cancer cell will have a different electrical or magnetic field from the ambient, healthy cells. Thus, to detect this type of anomaly in a human or animal body, the system of the present invention is connected as follows: The crystal 3 is connected to the semiconducting polymer 76 and the semiconducting polymer is attached into a hole; the hole is coated with metal, and hole is connected to the wire by the metal coating.

An outer electrical and magnetic field can change the orientation of the crystals and this changes the orientation of the crystals and this produces an electrons in the polymer, a metal strip between the metal coat in the hole and the wire leading to the voltmeter leads the electron to the wire connected with the collecting rail.

In one contemplated application, the circuit 100 of the present invention is energized from the power source 90, the parallel wires 72 have a known voltage, which applies a first or initial orientation to the crystal 3 in each cell. Then, the circuit is subjected to an external magnetic field or electrical, this changes the voltage in the wires 72, which in turn causes the crystal 3 in each cell to change orientation to a second position, resulting in the release or capture of an electron (depending on the crystal's properties and nature and direction of the field). Because the magnetic field is weak, the change by the position of the crystal 3 alters the ionic state of the semiconducting polymer 76 (hydrogel), which in turn changes the charge in the piece of metal wire 78 embedded in the cell 70. Thus, by measuring the change in voltage (see, e.g. FIG. 8) the circuit can detect that it has been subjected to a weak magnetic or electric field. In use, the circuit would be used to detect this change caused by the environment or application of use. To enhance the reliability of detecting change in voltage, the circuit could be cryogenically cooled, as is understood in the art.

One application of use would include mineral exploration. For example, the ambient level would be first recorded and then the circuit would be moved to a new location and any changes in voltage would be detected. The vain of a mineral or crystal, diamond, for example, Essentially, the background magnetic field is established by a base reading in the earth at a particular exploration site. Then, the circuit is moved along a predetermined route in that location and measuring the change orientation field in microchip, we will able to detect a mineral.

A second of use is to detect cancer cells, a biological sample material will have a certain base signature, cancer cells will have a different signature, this change will be recorded as a change in voltage in the circuit.

The present invention is illustrated as a one-layer array of sixteen cells: However, those skilled in the art will appreciate that additional layers may be stacked upon each other and the array may be expanded or reduced in size. Further, there may be an odd-number or rows and an even-number of columns, or vice versa. A single cell would be a one by one array, for example, but a two by one array would also work, and so on.

The present invention is well suited to detect very weak magnetic fields and electrical fields: Thus, its applications are far broader than the representative use examples discussed herein.

Although the invention has been particularly shown and described with reference to certain embodiments, it will be understood by those skilled in the art that various changes in form and detail may be made without departing from the spirit and scope of the invention.

We claim:

1. A circuit for detecting weak magnetic or weak electrical fields, the circuit comprising:
   at least one cell comprising a crystal having magnetic activity embedded in a first semiconducting polymer and a piece of wire coupled to the first semiconducting polymer;
   the cell insulated in a layer of a second polymer;
   at least one pair of wires running parallel to the cell arranged on opposite sides of the cell; and
   a voltage source to supply a first voltage in the pair of wires.

2. The circuit of claim 1, further comprising:
   a plate, the plate having at least one groove, the groove defining a first direction;
   the at least one pair of wires comprising a first wire running in the first direction parallel to the groove;
   the second polymer further embedding the first wire relative to the groove;
   a first lead running in a second direction perpendicular to the groove and the first lead electrically coupling to the first wire and further coupling to the voltage source;
   a second lead running in the second direction disposed on the plate opposite from the first lead, the second lead further coupling to the voltage source whereby the voltage is established in the pair of wires.

3. The circuit of claim 1 further comprising: a plurality of cells arranged in an array.

4. The circuit of claim 3 wherein: the array is a four by four array comprising sixteen cells, each cell comprising a corresponding crystal embedded in the corresponding first semiconducting polymer and the corresponding piece of wire coupled to the first semiconducting polymer.

5. The circuit of claim 1 wherein the first semiconducting polymer is an intrinsically conducting polymer (ICP).

6. The circuit of claim 1 wherein the second polymer is a hydrogels.

7. The circuit of claim 1 wherein the second polymer is a hydrogel comprising any one of the group consisting of Polyethylene glycol, or PolyAMPS.

8. The circuit of claim 1 further comprising: a voltmeter comprising a first lead coupled to the piece of wire of the cell and a second lead to couple to one wire of the pair of wires.

9. The circuit of claim 1 wherein the crystal comprises: a material selected from the group consisting of Ferroso-Ferric Oxide, Ferrous Oxide, Sulfur Oxide, $FeO_2$, or $FeSO_2$.

\* \* \* \* \*